United States Patent [19]
Laurencin et al.

[11] Patent Number: 6,077,916
[45] Date of Patent: Jun. 20, 2000

[54] BIODEGRADABLE MIXTURES OF POLYPHOSHAZENE AND OTHER POLYMERS

[75] Inventors: Cato Laurencin, Elkins Park; Harry Allcock, State College, both of Pa.; Sobrasua Ibim, Forrest Park, Ga.; Archel Ambrosio, Philadelphia; Michael Kwon, Narberth, both of Pa.

[73] Assignee: The Penn State Research Foundation, University Park, Pa.

[21] Appl. No.: 09/090,374

[22] Filed: Jun. 4, 1998

Related U.S. Application Data

[60] Provisional application No. 60/048,523, Jun. 4, 1997.

[51] Int. Cl.$^7$ .................................................. C08F 283/00
[52] U.S. Cl. .................. 525/419; 525/420; 525/903; 525/937; 525/938; 424/426; 424/422; 424/423; 424/484; 424/486; 604/27; 604/48
[58] Field of Search .................................. 525/419, 420, 525/903, 937, 938; 424/426, 422, 423, 484, 486; 604/27, 48

[56] References Cited

U.S. PATENT DOCUMENTS

| | | |
|---|---|---|
| 4,005,520 | 2/1977 | Sanford . |
| 4,061,606 | 12/1977 | Dieck et al. . |
| 4,073,824 | 2/1978 | Dieck et al. . |
| 5,250,626 | 10/1993 | Landry et al. . |
| 5,308,701 | 5/1994 | Cohen et al. . |
| 5,562,909 | 10/1996 | Allcock et al. . |

OTHER PUBLICATIONS

Allcock, et al., "Poly[{amino acid ester) phosphazanes] as substrates for the controlled release of small molecules," *Biomaterials* 15(8):563–569 (1994).

Allcock, et al., "Hydrolysis pathways for aminophosphazenes," *Inorg. Chem.*, 21:515–521 (1982).

Allcock, et al., "Synthesis of poly[(amino acid alkyl ester) phosphazenes]," *Macromolecules*, 10:824–830 (1977).

Coombes, et al, "Gel casting of resorbable polymers: Processing and applications," *Biomaterials*, 13(4):217–24 (1992).

Crommen, et al., "Biodegradable polymers: I. Synthesis of hydrolysis–sensitive poly[(organo)phospazenes]," *Biomaterials* 13(8):511–520 (1992).

Dobry et al., "Phase Separation in Polymer Solution," *J. Polymer Sci.*, 2:90–97 (1947).

Eggli, et al., "Porous hydroxyapatite and tricalcium phosphate cylinders with two different pore size ranges implanted in the cancerous bone of rabbits", *Clin. Orthop.*, 232, 127–138 (1987).

Friedlaender, "Current Concepts Review: Bone Grafts," *J. of Bone and Joint Surgery*, 69A(5):786–90 (1987).

Goethals, editor, *Concise Encyclopedia of Polymer Science and Polmeric Amines and Ammonium Salts*, Pergamen Press: Elmford, NY 1980.

IBIM, et al., "Novel polyphosphazene/poly(lactide–co–glycolide) blends: miscibility and degradation studies," *Biomaterials* 18(23):1565–9 (1997).

Klawitter, et al., "Application of porous ceramics for the attachment of load bearing orthopedic applications", *J. Biomed. Mater. Res. Symp.*, 2:161 (1971).

Laurencin, et al., "Polymeric Controlled Release Systems: New Methods for Drug Delivery," *Clin Lab Med.* 7(2):301–23 (1987).

Laurencin, et al., Use of polyphosphazenes for skeletal tissue regeneration. *J. Biomed. Mater. Res.*, 27:963–73 (1993).

March, *Advanced Organic Chemistry*, 4th ed., Wiley–Interscience Publication: New York, 1992.

Waldvogel, in *Orhtopaedic Infection*, pp. 1–8 Springer–Verlag: New York, 1988.

White, et al., "Biomaterial aspects of Interpore 200 porous hydroxyapatite", *Dental Clinical of N. Amer.*, 30:49–67 (1986).

*Primary Examiner*—Duc Truong
*Attorney, Agent, or Firm*—Arnall Golden & Gregory, LLP

[57] ABSTRACT

Biodegradable polymeric compositions are provided, wherein biodegradable polyphosphazenes are combined with at least one other polymer, either in the form of a blend, a semi-interpenetrating network (semi-IPN), or an interpenetrating network IPN. The side groups and composition of the polyphosphazenes are used to determine the properties of the compositions, for example, the rate and extent of degradation, and mechanical properties. These are useful in biomedical applications, including controlled drug delivery and tissue regeneration, and environmental applications. In the most preferred embodiment, as demonstrated by the examples, the polyphosphazenes contain hydrophobic side groups, such as p-methylphenoxy and other aromatic groups, and groups which impart hydrolytic instability, such as amino acid alkyl esters, and degrade by surface erosion. A preferred example is ethyl glycinato-substituted polyphosphazene (PPHOS) with p-methylphenoxy as co-substituent. These are blended with other polymers, such as PLGA, which have desirable mechanical properties but which degrade by bulk erosion, so that the blend degrades by surface erosion. For the biomedical applications, FDA approved polymers, such as polymers of lactic and glycolic acids and their copolymers, are preferred. Methods for making these compositions also are provided.

17 Claims, No Drawings

6,077,916

BIODEGRADABLE MIXTURES OF POLYPHOSHAZENE AND OTHER POLYMERS

CROSS-REFERENCE TO RELATED APPLICATIONS

Priority is claimed to U.S. Provisional Application Ser. No. 60/048,523, filed Jun. 4, 1997.

STATEMENT REGARDING FEDERALLY FUNDED RESEARCH

The U.S. Government has certain rights by virtue of NIH Grant No. AR41972 to Cato Laurencin.

BACKGROUND OF THE INVENTION

This invention is generally in the field of polymer blends, interpenetrating networks (IPN) of polymers, and semi-interpenetrating networks (semi-IPNs) of polymers, specifically those including polyphosphazene, for use in controlled degradation applications, such as biomedical applications.

The ability to regulate the rate and extent of degradation of a material is critical in many environmental and biomedical applications. In recent years, major research efforts have been directed towards the development of biodegradable materials for biomedical applications such as controlled drug delivery and tissue regeneration. The field of controlled drug delivery has evolved in an effort to overcome the many limitations of traditional drug delivery. Conventional parenteral drug delivery relies on repeated injection or infusion via different routes to achieve tissue levels of desired drugs. Consequently, patient compliance can be unsatisfactory. Waldvogel, in *Orthopaedic Infection*, Springer-Verlag: New York (1988) pp. 1–8. In addition, repeated injection or infusion leads to high serum levels of the drug, thus posing serious toxicity risks to otherwise healthy organ systems. Furthermore, wastage and costs can be considerable, because a substantial amount of the drug does not reach the target site.

By the 1950's technology had developed to successfully administer drugs at controlled rates using polymeric devices as the drug carriers. Laurencin and Langer, *Clinics in Lab. Med.* 7:301 (1987). Biodegradable, biocompatible matrices for controlled drug delivery provide many benefits. First, patient compliance is enhanced due to less frequent drug administration. Second, the risk of drug concentrations reaching toxic levels is minimized since the drug is released at controlled rates. Third, the cost of treatment is considerably reduced, because a smaller amount of drug can be used. Finally, in cases where the delivery device is surgically implanted, the need for a second surgical procedure in order to remove the drug-depleted device is obviated.

While biodegradable polymers, such as poly(lactide-co-glycolide) (PLGA), are useful in drug delivery and tissue regeneration applications since they degrade into harmless substances, drawbacks—primarily that they degrade by bulk erosion—limit their application. These polymers do not allow for release of a substance as controllable as is desired in certain controlled drug delivery applications. Since polymers of lactic and glycolic acids and their copolymers (PLGA) degrade quickly in the body into non-toxic products, PLGA is used for biodegradable sutures and can potentially be used in implantable screws, intravascular stents, pins, drug delivery devices, and as a temporary scaffold for tissue and bone repair. Additionally, PLGA has good mechanical properties which improve the structural integrity of such devices. However, since PLGA degrades completely by bulk erosion, it loses more than 50% of its mechanical strength in less than two months, which can lead to uncontrollable release rates of drugs and can develop biocompatibility problems (probably due to an accumulation of lactic and glycolic acids during degradation).

Other applications are also dependent on the rate and extent of degradation. For example, plastic medical devices, food containers, bottles, bags, and other materials currently in use create an extensive, expensive waste disposal problem. It is therefore highly desirable to create biodegradable materials that retain sufficient mechanical strength over the desired time period, but which degrade when no longer useful.

Accordingly, it is an object of this invention to provide biodegradable polymer mixtures for use in biomedical and environmental applications.

It is another object of this invention to provide biodegradable polymeric matrices which degrade by surface erosion.

It is another object of this invention to provide biodegradable polymeric matrices for which one can modulate the degradation rate.

It is another object of this invention to provide biodegradable polymeric matrices with a sufficient degree of flexibility to facilitate molding of the polymeric matrix.

It is another object of this invention to provide biodegradable, biocompatible polymeric matrices for controlled drug delivery and bone repair applications.

It is another object of this invention to provide biodegradable, biocompatible polymeric matrices with good osteoconductivity to aid in drug delivery to sites within bone.

It is another object of this invention to provide biodegradable polymeric matrices which degrade by bulk erosion for environmental uses.

SUMMARY OF THE INVENTION

Biodegradable polymeric compositions are formed by combining biodegradable polyphosphazenes and at least one other polymer, either in the form of a blend, a semi-interpenetrating network (semi-IPN), or an IPN. The side groups and composition of the polyphosphazenes are used to determine the properties of the compositions, for example, the rate and extent of degradation, and mechanical properties. These compositions are useful in biomedical applications, including controlled drug delivery and tissue regeneration, and environmental applications.

In the most preferred embodiment, as demonstrated by the examples, the polyphosphazenes contain hydrophobic side groups, such as p-methylphenoxy and other aromatic groups, and groups which impart hydrolytic instability, such as amino acid alkyl esters, and degrade by surface erosion. A preferred example is ethyl glycinato-substituted polyphosphazene (PPHOS) with p-methylphenoxy as co-substituent. These polyphosphazenes are blended with other polymers, such as PLGA, which has desirable mechanical properties but which degrades by bulk erosion, so that the blend degrades by surface erosion. Any polymer which degrades by bulk or surface erosion can be used. However, for the biomedical applications, FDA approved polymers, such as polymers of lactic and glycolic acids and their copolymers, are preferred.

DETAILED DESCRIPTION OF THE INVENTION

The compositions have essentially two main components: one or more biodegradable polyphosphazenes and one or more other polymers. Additional components, depending on the application for which the composition is intended, include drugs, imaging agents, cells, coatings, pore forming agents, plasticizers, and cross-linkers. The compositions are typically formed by blending. Semi-IPNs or IPNs may then be formed by crosslinking, using standard techniques. The polyphosphazenes can be tailored to be compatible with, or alter the properties of, a wide variety of polymers by changing the side groups. A polyphosphazene with hydrophobic side groups and side groups that impart hydrolytic instability can be mixed with a polymer which degrades by bulk or surface erosion to yield a polymer which degrades by surface erosion. Alternately, the polyphosphazene may have a side group which is both hydrophobic and imparts hydrolytic instability to acheive the same result. Such mixtures are useful in biomedical and environmental applications which require controlled degradation rates.

I. POLYMERS

A. Definitions

The term "miscible blend" as used herein describes a blend which exhibits a single glass transition temperature ($T_g$). These blends do not undergo phase separation.

The term "polyphosphazene" as used herein describes a polymer with a backbone consisting of nitrogen and phosphorus separated by alternating single and double bonds. Each phosphorus atom is covalently bonded with two side chains ("R"). The repeat unit has the general structure of (1):

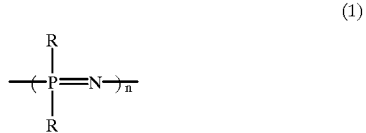

(1)

wherein n is an integer.

The term "surface erodible" as used herein describes any material which degrades uniformly from the surface of the material, and therefore substantially maintains its original shape throughout the degradation process.

The term "bulk erodible" as used herein describes any material which degrades throughout the bulk of the material (i.e. at the surface and within its interior), to therefore permit or cause the material to collapse, or fall apart, following partial degradation.

Biodegradable polymers are those that have a half life under physiological conditions of between about two hours and one year.

Non-biodegradable polymers are those that have a half life longer than approximately one year under physiological conditions.

Interpenetrating networks (IPNs) are matrices containing two polymers in which each of the polymers is crosslinked to itself or in which the polymers are crosslinked to each other.

Semi-interpenetrating networks (semi-IPNs) are matrices containing two polymers in which only one of the polymers is crosslinked. These matrices can be formed by swelling a crosslinked polymer with a monomer of a second polymer and then polymerizing the second polymer.

B. Polyphosphazenes

Polyphosphazenes are high molecular weight polymers with an inorganic backbone of alternating phosphorus and nitrogen atoms with two side groups on each phosphorus atom. Polymers with a wide range of properties can be synthesized from this polymer backbone by incorporating different side groups, by varying the side group in single-substituent polyphosphazenes, and/or by using two or more co-substituents. Individual polyphosphazenes may be hydrophobic, amphiphilic, or hydrophilic; water-stable or water-erodible; crystalline or amorphus; bioinert or bioactive. The hydrophobicity of the polyphosphazene is increased by adding hydrophobic side groups, such as aromatic groups, to the backbone. One can regulate the degradation rate by increasing the hydrophobicity of the polyphosphazene.

Examples of polyphosphazenes which degrade by surface erosion and which can be used to make the desired blends contain hydrophobic side groups and groups which impart hydrolytic instability. The hydrophobic side groups include, but are not limited to, aromatic groups, such as p-methylphenoxy. Side groups that impart hydrolytic instability include, but are not limited to, amino acid alkyl esters.

For example, the hydrophobicity of an ethyl glycinato-substituted polyphosphazene (PPHOS) is increased by adding p-methylphenoxy as co-substituent. The ethyl glycinato side group imparts biodegradability to the molecule. This molecule degrades in aqueous environments to produce innocuous products. PPHOS has been found to support the adhesion and growth of osteoblast-like cells, a beneficial property for bone repair applications. Laurencin, et al., *J. Biomed. Mater. Res.* 27:963 (1993).

Miscible blends within the same class of polyphosphazenes are described in U.S. Pat. Nos. 4,005,520 and 4,073,824 to Dieck, et al. These systems are limited to mixtures within the same family of polyphosphazenes. However, they could be mixed with other polymers as described herein. Miscible blends of etheric polyphosphazenes and polymers bearing acidic functional groups are described in U.S. Pat. No. 5,250,626 to Landry, et al. However these blends are not biodegradable and therefore are not suitable for biomedical nor environmental applications.

C. Non-polyphosphazene Polymers

Biodegradable or non-biodegradable polymers can be used. Polymers which degrade by either bulk or surface erosion can be used. Mixtures of these polymers can be mixed with polyphosphazene. For biomedical applications, polymers which have received FDA approval, such as polylactide, polyglycolide, and blends and copolymers thereof are preferred.

For medical applications, it is preferable that the polymer degrades after the treatment period ends. The degradation products of the polymer in these medical applications should have a sufficiently low molecular weight to allow excretion. A low initial molecular weight of the polymer should aid in blend formation.

Hydrophobic polymers are well known to those of skill in the art. Examples of hydrophobic biodegradable polymers include polyanhydrides, polyorthoesters, polyhydroxy acids, polydioxanones, polycarbonates, and polyaminocarbonates. Examples of hydrophobic non-biodegradable polymers include polyethylene, polypropylene, poly(acrylic acid), poly(methacrylic acid), and some polyesters.

Examples of hydrophilic non-biodegradable polymers include poly(ethylene glycol), poly(ethylene oxide), partially or fully hydrolyzed poly(vinyl alcohol), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll® polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof.

The polymers must have crosslinkable groups to form IPNs. Suitable polymerizable groups include ethylenically unsaturated groups (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. The preferred polymerizable groups are acrylates, diacrylates, oligoacrylates, dimethacrylates, oligomethacrylates, and other biologically acceptable photopolymerizable groups. (Meth)acrylates are the most preferred active species polymerizable group. These functional groups can be present on the polymers, or added as monomers to the polymer mixture.

Methods for the synthesis of these polymers are well known to those skilled in the art. See, for example, *Concise Encyclopedia of Polymer Science and Polymeric Amines and Ammonium Salts*, E. Goethals, editor (Pergamen Press, Elmsford, N.Y. 1980). Many polymers, such as PLGA and poly(acrylic acid), are commercially available. Naturally occurring and synthetic polymers may be modified using chemical reactions available in the art and described, for example, in March, "Advanced Organic Chemistry," 4th ed., Wiley-Interscience Publication, New York (1992).

II. METHODS FOR MAKING BLENDS AND IPNs

A. Blends

Blends can be formed by co-dissolving the polymers in a solvent, by melting and mixing the two polymers, or other standard techniques. The polymers can be dissolved in a solvent that does not adversely affect or react with the polymers or any material or particles to be suspended in the solution. The relative amount of solvent will have a minimal effect on the structure of the polymer blend, but will affect the solvent evaporation time.

Solvents should be non-reactive with the components of the composition. It is preferable that no protic solvents are used since hydrolyzable linkages are present. Halogenated solvents may be used in those embodiments where the composition is polymerized ex vivo, or where the solvents can be effectively removed prior to implanting the articles. It is preferred to use solvents which are non-toxic for in vivo applications. Suitable solvents for these applications include glyme, dimethylsulfoxide (DMSO) and other polar aprotic solvents.

A solution or dispersion of the polymer mixture can be cast, extruded or injected into any appropriate mold. The solvent is then evaporated from the composition over a period of time, for example, 24 hours at room temperature. Any residual solvent can be subsequently removed by lyophilization.

Polymers can be blended in any ratio which yields the desired properties. This ratio can range from 1 to 99, polyphosphazene to polymer, to 99 to 1, polyphosphazene to polymer. A more preferred ratio is 25:75, polyphosphazene to other polymer.

B. IPNs or Semi-IPNs

Interpenetrating networks are formed by crosslinking some or all of the polymers in the mixture. This can be used to impart additional stability.

The polymers can be polymerized using any suitable free-radical initiators (active species), for example, photoinitiators and thermally activatable initiators (preferably in a concentration not toxic to cells, less than 1% by weight, more preferably between 0.05 and 0.01% by weight percent initiator). The polymers form semi-interpenetrating polymer networks when crosslinked.

The compositions can be polymerized ex vivo to provide solid articles, such as pins and screws, which can be used to repair bones. Alternatively, the compositions can be polymerized in situ to function as a bone cement. For those areas which can be accessed via injection, the composition is preferably fluid when applied, and solid when polymerized.

"Electromagnetic Radiation", as used herein, refers to energy waves of the electromagnetic spectrum including, but not limited to, x-ray, ultraviolet, visible, infrared, far infrared, microwave, and radio-frequency, and can be used to crosslink the polymers.

"Visible light" refers to energy waves having a wavelength of at least approximately $4.0 \times 10^{-5}$ cm. "Ultraviolet light" refers to energy waves having a wavelength of at least approximately $1.0 \times 10^{-5}$ cm but less than $7.0 \times 10^{-5}$ cm. "Blue light" as used herein refers to energy waves having a wavelength of at least approximately $4.5 \times 10^{-5}$ cm but less than $4.9 \times 10^{-5}$ cm. The polymers can be crosslinked by exposure to a radiation source, such as lamps, the sun, blue lamps, and ultraviolet lamps.

Suitable thermally activatable initiators include various peroxides and azobisisobutyronitrile (AIBN). Suitable photoinitiators include those photoinitiators that are capable of crosslinking the composition upon exposure to light equivalent to between 0.01 mW/cm$^2$ and 1 Watt/cm$^2$. A minimum of 0.01 mW/cm$^2$ intensity is needed to induce polymerization. Maximum light intensity can range from one to 1000 mW/cm$^2$, depending upon the wavelength of radiation. Photoinitiators that generate an active species on exposure to UV light are well known to those of skill in the art.

Tissues can be exposed to higher light intensities, for example, longer wavelength visible light, which causes less tissue/cell damage than shortwave UV light. In dental applications, blue light (470–490 nm) is used at intensities of 100 to 400 mW/cm$^2$ clinically.

Preferably, when the crosslinking occurs in vivo, the polymerization conditions are mild enough not to damage surrounding tissue. Although discussed herein principally with regard to administration of a light source external to the skin, this should be interpreted as equally applicable to light applied through tissues, for example, from a catheter in a blood vessel adjacent to where the composition has been injected, or in the space adjacent to a bone to be repaired. The depth of penetration can be controlled by the wavelength of the light used to cause the photopolymerization. For example, visible light penetrates deeper through tissue than UV light. Penetration through tissue can range from microns to one cm, with one cm occurring with visible light. In a preferred embodiment, radiation with a wavelength between 200 and 700 nm is used to create active species and polymerize the network.

The polymerizable groups in the composition can be polymerized using photoinitiators that generate active species upon exposure to UV light, or, preferably, using long-wavelength ultraviolet light (LWUV) or visible light, for example, by photon absorption of certain dyes and chemical compounds. LWUV and visible light are preferred because they cause less damage to tissue and other biological materials than UV light. Useful photoinitiators are those which can be used to initiate polymerization of the macromers without cytotoxicity and within a short time frame, minutes at most and most preferably seconds.

Exposure of dyes and cocatalysts such as amines to visible or LWUV light can generate active species. Light absorption by the dye causes the dye to assume a triplet state, and the triplet state subsequently reacts with the amine to form an active species which initiates polymerization. Polymerization can be initiated by irradiation with light at a wavelength of between about 200–700 nm, most preferably in the long wavelength ultraviolet range or visible range, 320 nm or higher, and most preferably between about 365 and 514 nm.

Numerous dyes can be used for photopolymerization. Suitable dyes are well known to those of skill in the art. Preferred dyes include erythrosin, phloxime, rose bengal, thonine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable cocatalysts include amines such as N-methyl diethanolamine, N,N-dimethyl benzylamine, triethanol amine, triethylamine, dibenzyl amine, N-benzylethanolamine, N-isopropyl benzylamine. Triethanolamine is a preferred cocatalyst.

C. Additives

A number of different additives can be added to the blend during formation.

Porosity Forming Agents

The polymer mixtures can also include various inorganic or volatile salts and/or proteinaceous materials, such as gelatin, which dissolve at a relatively faster rate under physiological conditions than the composition. The removal of these particles creates pores in the polymer mixture. The materials can be selected to have a desired size or size distribution, and can be evenly distributed throughout the composition to provide controlled porosity.

Suitable materials include particles of salts. For tissue engineering devices, the particles can be any salt that forms crystals or particles having a diameter of approximately 100 to 250 microns, which is easily removed from and does not react with the polymer, and is non-toxic if some residue remains in the polymer after leaching. Micro- or nano-particles of degradable polymer can also be used to provide porosity, if they degrade at a faster rate than the blend or crosslinked composition. Examples of other porosity forming agents include proteins such as gelatin and agarose, starches, polysaccharides such as alginate and other polymers. Preferably, the salt is a sodium salt, such as sodium chloride, sodium tartrate and sodium citrate, and other water soluble salts not soluble in the polymer solvent, for example, tetrahydrofuran. The most preferred salt is sodium chloride. Preferably, the particles are first sieved through a mesh or a series of screens to provide particles of relatively uniform diameter. The particles are then added to the composition. The initial weight fraction of porosity forming agents is preferably between 0.02 and 0.9 dry weight percent. The initial weight fraction is instrumental in determining the characteristics of the semi-interpenetrating polymer matrix.

A particulate leaching process can be used to create a porous polymeric matrix. In one embodiment, salt particles are suspended in the polymer blend, the solvent is removed, and the particles are leached out of the hardened polymer. When hydrolytically unstable groups are present, it is preferable to avoid using aqueous solutions to remove salts to create porosity.

Removal of the particles will create a polymer matrix having a plurality of relatively evenly spaced interconnected interstitial spaces or pores, formerly occupied by the particle crystals, into which cells can migrate, attach, and proliferate, or into which drugs can be dispersed. The porosity of the matrix can be very high, typically between 60 and 90%, depending on the amount of incorporated particles. Preferably, the pores in the composition can have a pore size in the range of between approximately 100 and 250 microns, by appropriate selection of the size of the leachable particles.

An interconnecting pore network is described by H. R. Allcock, et al., "Synthesis of poly[(amino acid alkyl ester) phosphazenes]," *Macromolecules*, 10, 824–830 (1977); H. R. Allcock, et al., "Hydrolysis pathways for aminophosphazenes," *Inorg. Chem.*, 21, 515–521 (1982); and Eggli, P. S., et al., "Porous hydroxyapatite and tricalcium phosphate cylinders with two different pore size ranges implanted in the cancerous bone of rabbits", *Clin. Orthop.*, 232, 127–138 (1987). Such a network facilitates the invasion of cells and promotes an organized growth of the incoming cells and tissue. The polymer described by Allcock, et al. can be replaced with the polymer mixtures described herein. The porosity has been demonstrated to influence the biocompatibility and bony integration on various porous material. White and Shors, "Biomaterial aspects of Interpore 200 porous hydroxyapatite", *Dental Clinical of N. Amer.*, 30, 49–67 (1986). Klaitwatter, et al., "Application of porous ceramics for the attachment of load bearing orthopedic applications", *J. Biomed. Mater. Res. Symp.*, 2, 161 (1971) shows that a pore size of over a 100 $\mu$m is suitable and necessary for regenerating cells and bony ingrowth.

Excipients

The compositions can also include particles of excipients, for example, ceramics. Specific excipients include hydroxyapatite, plaster of paris, calcium carbonate, tricalcium phosphate, polyphosphates, polyphosphonates, and polyphosphites.

Therapeutic Agents

The compositions can also include various therapeutic and/or diagnostic agents. The agents can be incorporated in the composition directly, or can be incorporated in microparticles which are then incorporated into the composition. Incorporating the agents in microparticles can be advantageous for those agents which are reactive with one or more of the components of the composition, i.e. agents which have hydroxy or amine functionality which are incorporated into compositions including anhydride linkages. Microparticles, and methods of preparation thereof, are well known to those of skill in the art.

Examples of therapeutic agents which can be incorporated into the compositions include proteins, polysaccharides, nucleic acid molecules, and synthetic organic or inorganic molecules. Proteins are defined as consisting of 100 amino acid residues or more; peptides are less than 100 amino acid residues. Unless otherwise stated, the term protein refers to both proteins and peptides. Examples include insulin and other hormones. Polysaccharides, such as heparin, can also be administered. Compounds with a wide range of molecular weight, for example, between 50 and 500,000 grams per mole, can be incorporated into the composition. These may be useful for therapeutic or diagnostic purposes. Nucleic acid molecules include genes, antisense molecules which bind to complementary DNA to inhibit transcription, ribozymes and ribozyme guide sequences. Drugs which can be used include anaesthetics, antibiotics, antivirals, genes, chemotherapeutic agents, anti-angiogenic agents, hormones, drugs having an effect on vascular flow, growth factors, and anti-inflammatories.

The compositions can be combined with humoral factors to promote cell transplantation and engraftment. For example, the compositions can be combined with angiogenic factors, antibiotics, anti-inflammatories, growth factors, compounds which induce differentiation, and other factors which are known to those skilled in the art of cell culture.

Diagnostic Agents

Any of a variety of diagnostic agents can be incorporated within the compositions, which can locally or systemically deliver the incorporated agents following administration to a patient. Imaging agents can be used which allow one to monitor bone repair following implantation of the compositions in a patient. Suitable imaging agents include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include the gadolinium chelates currently available, such as diethylene triamine pentaacetic acid (DTPA) and gadopentotate dimeglumine, as well as iron, magnesium, manganese, copper, and chromium.

Examples of materials useful for CAT and x-rays include iodine based materials, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

Air and other gases can be incorporated for use in ultrasound imaging. These agents can be detected using standard techniques available in the art and commercially available equipment.

D. Formation of Bone Prosthetics and Other Implants

Successful design of an implant to replace skeletal tissue requires knowledge of the structure and mechanical properties of bone and an understanding of the means by which grafts become incorporated into the body. This information can then be used to define desirable characteristics of the implant to ensure that the graft functions in a manner comparable to organic tissue. A graft may be necessary when bone fails and does not repair itself in the normal amount of time or when bone loss occurs through injury or cancer. Bone grafts must serve a dual function: to provide mechanical stability and to be a matrix or environment for osteogenesis. Since skeletal injuries are repaired by the regeneration of bone rather than by the formation of scar tissue, grafting is a viable means of promoting healing of osseous defects, as reviewed by Friedlaender, G. E., "Current Concepts Review: Bone Grafts," *J. of Bone and Joint Surgery*, 69A(5), 786–90 (1987). Osteoinduction and osteoconduction are two mechanisms by which a graft may stimulate the growth of new bone. In the former case, inductive signals lead to the phenotypic conversion of connective tissue cells to bone cells. In the latter, the implant provides a scaffold for bony ingrowth.

The bone remodeling cycle is a continuous event involving the resorption of pre-existing bone by osteoclasts and the formation of new bone by the work of osteoblasts. Normally, these two phases are synchronous and bone mass remains constant. However, the processes become uncoupled when bone defects heal and grafts are incorporated. Osteoclasts resorb the graft, a process which may take months. More porous grafts revascularize more quickly and graft resorption is more complete. Bone formation begins after the graft has been resorbed. Bone mass and mechanical strength return to near normal.

Synthetic implants formed of the polymeric mixtures described herein may obviate many of the problems associated with organic grafts. Further, synthetics can be produced in a variety of stock shapes and sizes, enabling the surgeon to select implants as his needs dictate, as described by Coombes, A. D. A. and J. D. Heckman, "Gel Casting of Resorbable Polymers: Processing and Applications," *Biomaterials*, 13(4):217–24 (1992). Metals, calcium phosphate ceramics and polymers have all been used in grafting applications.

The polymeric matrices can be designed for use in types of organ or tissue implantation or regeneration, other than bone, including growth and/or implantation of nerve cells, muscle, bone, cartilage or tendon, and mesenchymal (cells having a metabolic function, such as liver, intestine, pancreatic, etc) cells.

The matrix described here is implanted using standard surgical technique. The matrix can be directly implanted into the site where growth is desired. In the preferred embodiment, the matrix will be pre-cast into a desired shape.

It is preferable for certain applications, for example when the composition is polymerized or solidified in situ, for the composition to be fluid enough to be injectable. Following injection into a site in a patient, the composition can be crosslinked and/or solvent removed to form a solid polymer network.

The composition can be used as a bulking agent for hard tissue defects, such as bone or cartilage defects. Examples include injection of the composition into the area surrounding the skull where a bony deformity exists secondary to trauma, or, in the case of complex fractures of long bones, such as the femur or tibia, injection or implantation into the bone or area of bone loss or fragmentation. The composition can also be used in reconstructive surgery.

For use in dental applications, the viscosity of the composition is preferably thick, or paste-like, such that it can be applied to the surface of a broken tooth such that the composition will maintain a desired shape, and will harden when solvent is removed or when the mixture polymerized. The viscosity can be adjusted by adding appropriate viscosity modifying agents.

The present invention will be further understood by reference to the following non-limiting examples.

EXAMPLE 1

Fabrication of PPHOS/PLGA Blends

The mutual solvent approach was used to make cohesive miscible blends which retain the desirable properties of both parent polymers. Dobry and Boyer-Kawenoki, "The mutual solvent approach", *J. Polymer Sci.*, 2:90–97 (1947). A polymer was synthesized by blending PLGA and PPHOS to yield a compositions with the beneficial features of its components: PLGA's biocompatibility and widespread applicability and PPHOS's hydrophobicity.

Synthesis of Ethyl Glycinato-substituted Polyphosphazenes (PPHOS)

Polyphosphazenes are formed by reacting poly (dichlorophosphazene) with the appropriate side chain nucleophiles, which displace the chlorines. Poly[(25% ethyl glycinato)(75% p-methylphenoxy) phosphazene] (PPHOS-25), poly[(50% ethyl glycinato)(50% p-methylphenoxy) phosphazene] (PPHOS-50) and poly[(75% ethyl glycinato) (25% p-methylphenoxy) phosphazene] (PPHOS-75) were synthesized according to a procedure reported by Laurencin, et al., Use of polyphosphazenes for skeletal tissue regeneration. *J. Biomed. Mater. Res.*, 1993, 27, 963–73. Briefly, poly(dichlorophosphazene) was allowed to react with sodium p-methylphenoxide in order to replace 75%, 50% or 25% of the chlorine atoms. The partially substituted polyphosphazenes were then allowed to react with a large excess of ethyl glycinate to replace the remaining chlorine atoms and obtain the fully substituted polyphosphazenes. The polyphosphazenes were purified by repeated precipitations in heptane (five times) followed by centrifugation in order to remove residual salts. The polyphosphazenes were dried under vacuum and stored under argon prior to use.

Fabrication of Blend

Blend A (PLGA/PPHOS-25), Blend B (PLGA/PPHOS-50) and Blend C (PLGA/PPHOS-75) were fabricated using the mutual solvent approach. First, 0.5 g of PLGA and 0.5 g of PPHOS were blended in glass scintillation vials containing 10 mL of chloroform and mixed vigorously for 24 h until dissolved. Following dissolution and further vortexing for another 4 h, the solutions were allowed to stand at room temperature for at least 48 h to ensure that no phase separation occurred prior to casting the mixture. The mixtures were then poured into a plastic petri dish lined with Bytac TEFLON™ paper and air dried for 24 h. The blends were dried further by lyophilization (Labconco 12, Kansas City, Kans. USA) for at least 24 h and stored at −20° C. until used.

Miscibility of Blend

The miscibility of two different polymers in polymer blends is generally a result of strong intermolecular interactions between the polymers. These interactions include hydrogen bonding, dipole-dipole interactions, and van der Waals forces. Sometimes, the miscibility of polymers may be due mainly to entropic effects. In the case of PLGA and PPHOS polymers, their miscibility can probably be attributed to the presence of similar functional groups (ester groups) on both types of polymers which can enhance the intermolecular interactions (dipole-dipole and van der Waals) between the polymers. Additionally, strong hydrogen bonding can occur between the amino groups of the PPHOS polymers and the ester groups of PLGA.

The miscibility of the PPHOS/PLGA blend was determined by measuring the glass transition temperature ($T_g$) through differential scanning calorimetry (DSC), analyzing the surface characteristics using scanning electron microscopy (SEM), and measuring the degradation rates over a two week period. Each of the blends had a single glass transition temperature between the glass transition temperatures of their respective parent polymers. The surface analysis, using SEM, demonstrated that the blends have smooth, uniform surfaces. Additionally, the degradation studies showed near-zero order degradation kinetics for each of the blends, where Blends A and B lost 10% of their mass after 2 weeks, while Blends C lost 30% of its mass during the same time period.

The teachings of the cited publications are indicative of the level of skill and the general knowledge of those of skill in the art. To the extent necessary, the publications are specifically incorporated herein by reference. Modifications and variations of the present invention will be obvious to those skilled in the art from the foregoing detailed description and are intended to be encompassed by the following claims.

We claim:

1. A composition comprising a biodegradable polymeric mixture of a biodegradable polyphosphazene and a second polymer other than a polyphosphazene.

2. The composition of claim 1 wherein the second polymer is selected from the group consisting of hydrophobic polymers, hydrophilic polymers, and amphiphilic polymers.

3. The composition of claim 1 wherein the second polymer degrades by bulk erosion.

4. The composition of claim 1 wherein the second polymer degrades by surface erosion.

5. The composition of claim 1 wherein the mixture is a miscible blend.

6. The composition of claim 1 wherein the mixture is an interpenetrating network.

7. The composition of claim 6 wherein the polymers include crosslinkable groups.

8. The composition of claim 1 wherein the mixture further comprises an additive selected from the group consisting of porosity forming agents, therapeutic agents, diagnostic agents, and excipients.

9. The composition of claim 1 wherein the polyphosphazene is ethyl glycinato-substituted polyphosphazene with p-methylphenoxy as the co-substituent and the other polymer is poly(lactide-co-glycolide).

10. The composition of claim 1 shaped to form an implant for tissue repair or regeneration.

11. The composition of claim 10 further comprising a therapeutic or diagnostic agent.

12. The composition of claim 1 wherein the polyphosphazene contains hydrophobic side groups selected from the group consisting of aromatic groups, hydrophobic aminoacid alkyl esters, and long chain aliphatic groups.

13. The composition of claim 1 wherein the polyphosphazene contains side groups which impart hydrolytic instability.

14. The composition of claim 13 wherein the side group is an amino acid alkyl ester.

15. The composition of claim 1 wherein the polyphosphazene degrades by surface erosion.

16. A method for controlled drug delivery, the method comprising administering to a patient a composition comprising:

a biodegradable polymeric mixture of a biodegradable polyphosphazene and a second polymer other than a polyphosphazene; and a drug to be delivered.

17. A method for tissue regeneration, the method comprising implanting in a patient a tissue regeneration scaffold comprising a biodegradable polymeric mixture of a biodegradable polyphosphazene and a second polymer other than a polyphosphazene.

* * * * *